United States Patent [19]

Takaichi et al.

[11] Patent Number: 5,919,483
[45] Date of Patent: Jul. 6, 1999

[54] ANTIOXIDANT-CONTAINING EFFERVESCENT COMPOSITION

[75] Inventors: Akihisa Takaichi, Naruto; Toshihiko Okamoto; Toshiaki Matsumoto, both of Tokushima, all of Japan

[73] Assignee: Otsuka Pharmaceutical Co., Ltd., Tokyo, Japan

[21] Appl. No.: 08/617,841

[22] PCT Filed: Jul. 12, 1995

[86] PCT No.: PCT/JP95/01380

§ 371 Date: Mar. 13, 1996

§ 102(e) Date: Mar. 13, 1996

[87] PCT Pub. No.: WO96/02609

PCT Pub. Date: Feb. 1, 1996

[30] Foreign Application Priority Data

Jul. 15, 1994 [JP] Japan .................................. 6-163787

[51] Int. Cl.⁶ ...................................................... A61K 9/46
[52] U.S. Cl. ........................ 424/466; 424/451; 424/464; 424/489; 514/456; 514/725; 514/962
[58] Field of Search ..................... 424/466, 451, 424/464, 489; 514/960, 456, 725, 962

[56] References Cited

FOREIGN PATENT DOCUMENTS

A3517916   11/1986   Denmark .
A2083997    4/1982   United Kingdom .

OTHER PUBLICATIONS

Derwent Abstract of JP–A–59 166 585 (1984).

*Primary Examiner*—Raj Bawa
*Attorney, Agent, or Firm*—Sughrue, Mion, Zinn, Macpeak & Seas, PLLC

[57] ABSTRACT

This invention provides an antioxidant-containing effervescent composition comprising, as essential components, 0.05 to 15% by weight of an antioxidant-containing powder, 10 to 35% by weight of sodium hydrogencarbonate and/or sodium carbonate, 10 to 70% by weight of a neutralizing agent and 30 to 55% by weight of an excipient. The antioxidant-containing effervescent composition of the invention stably contains an antioxidant and is excellent in solubility.

6 Claims, No Drawings

ANTIOXIDANT-CONTAINING EFFERVESCENT COMPOSITION

TECHNICAL FIELD

The present invention relates to an antioxidant-containing effervescent composition

PRIOR ART

Antioxidants such as carotin, vitamin E, catechin or the like have been known to show activities, when combining with radicals occurring in vivo, of stabilizing the radicals, terminating the chain reaction of radicals in vivo (radical scavenger activity), and inhibiting the catabolism of organism-constituting protein and the like (antioxidation activity), thereby preventing carcinogenesis (anti-cancer activity). Recently, it has been reported that antioxidants also have an activity of hindering sunburn from developing by exposure to ultraviolet and an immunopotentiating activity. Attention is now focused on antioxidants useful as food materials and pharmaceutical materials in view of the current health food-oriented trend.

However, antioxidants are difficult to make into an effervescent preparation because of their solubility and stability to air (oxygen), light, heat, etc.

An object of the present invention is to provide a novel preparation, particularly a novel effervescent composition, which uniformly and stably contains said antioxidant and which is excellent in solubility.

DISCLOSURE OF THE INVENTION

The inventors of the present invention conducted extensive research and found that the foregoing object can be achieved by an effervescent composition containing the undermentioned specific antioxidant-containing powder. The present invention has been accomplished based on this novel finding.

According to the present invention, there is provided an antioxidant-containing effervescent composition comprising, as essential components:

0.05 to 15% by weight (hereinafter simply referred to as %) of either an antioxidant-containing powder containing 0.2 to 20% (based on the antioxidant-containing powder) of an antioxidant (fat-soluble substance) or catechin [a catechin-containing powder containing at least 10% (based on the catechin-containing powder) of a water-soluble antioxidant], 10 to 35% of sodium hydrogencarbonate and/or sodium carbonate, 10 to 70% of a neutralizing agent, and 30 to 55% of an excipient.

According to the inventions there are also provided said antioxidant-containing effervescent composition comprising, as essential components, 0.1 to 5.0% of an antioxidant-containing powder containing 0.5 to 10% (based on the antioxidant-containing powder) of an antioxidant (fat-soluble substance), 20 to 30% of sodium hydrogencarbonate and/or sodium carbonate, 10 to 40% of a neutralizing agent and 30 to 55% of an excipient; said antioxidant-containing effervescent composition, wherein the neutralizing agent is selected from malic acid, tartaric acid, citric acid and ascorbic acid; said antioxidant-containing effervescent composition, wherein the excipient is a carbohydrate selected from maltitol, sorbitol and maltose; and said antioxidant-containing effervescent composition, wherein said antioxidant is at least one member selected from the group consisting of carotin, vitamin E and catechin.

The antioxidant-containing effervescent composition of the present invention has features that the composition is capable of satisfactorily preventing the properties of the antioxidant from degrading due to oxidation and shows high solubility even in cold water.

The composition of the present invention will be described below in more detail. The antioxidant-containing powder as one of the essential components of said effervescent composition includes, for example, powders containing carotin, vitamin E, catechin or the like as an antioxidant. The carotin is a precursor of vitamin A and has a provitamin A activity Useful carotins include α-, β- and γ-carotins. The vitamin E can be any of α-, β-, γ- and δ-tocopherol. Said species of carotin and vitamin E, whether they are natural or synthetic, can be advantageously used in the practice of the invention. Typical examples of catechins are epigallocatechin gallates (EGCg), epicatechin gallates (ECg), epigallocatechins (EGC) and epicatechins (EC), such as tea polyphenol, apple polyphenol and the like.

Of the antioxidant-containing powders, powders containing carotin, vitamin E or like fat-soluble substances include, for example, those having a matrix comprising said antioxidant dissolved in a suitable fat and oil and a suitable base material (excipient) for forming particles, or an emulsifier or the like for solubilization. Examples of useful fats and oils include conventional fats and oils such as corn oil, peanut oil, essential oil and like vegetable fats and oils. Examples of base materials (excipients) for forming particles include conventional materials including saccharides such as lactose, gum arabic, dextrin, etc.; polysaccharides capable of functioning also as an emulsifier, such as gum arabic, casein, etc.; and proteins. Examples of useful emulsifiers are lecithin, glycerin ester of fatty acid, sucrose ester of fatty acid, calcium stearoyl lactate, sorbitan ester of fatty acid, propylene glycol ester of fatty acid, etc. The antioxidant-containing powder for use in the invention may contain an oxidation inhibitor for inhibiting the oxidation of carotin or like antioxidants in the powder, such as esters of L-ascorbic acid with palmitic acid, vitamin C, enzymatically modified rutin, etc. The incorporation of such oxidation inhibitor in the powder is desirable.

The matrix of the antioxidant-containing powder can be formed by conventional methods such as spray drying to give the desired powder having an optional particle size.

Of the antioxidant-containing powders, powders containing catechin or like water-soluble antioxidant can be easily prepared merely, for example, by extracting the antioxidant with hot water or alcohol, concentrating the extract, and making the concentrate into particles by conventional methods such as spray drying.

The proportion of the antioxidant-containing powder in the composition of the invention is in the range of 0.05 to 15%, preferably 0.1 to 5.0%. The proportion of the antioxidant (fat-soluble substance) in the powder is 0.2 to 20%, preferably 0.5 to 10%. This means that the balance 99.8 to 80% consists of the fat and oil, the base material for forming particles or emulsifier, and the oxidation inhibitor optionally added with these components. The oxidation inhibitor, when incorporated in the powder, is preferably used in a proportion of about 0.5 to about 20% of the antioxidant-containing powder. The proportion of catechin or like water-soluble antioxidant in the powder is at least 10%.

The other essential components for use in the invention are a combination of specific amounts of sodium hydrogencarbonate and/or sodium carbonate and a neutralizing agent as effervescent components, and a carbohydrate. The term "neutralizing agent" used herein refers to an acidic compound capable of producing carbon dioxide by neutralization of sodium hydrogencarbonate and/or sodium carbonate. Typical examples of such acidic compounds include L-tartaric acid, citric acid, lactic acid, dl-malic acid, fumaric acid, L-ascorbic acid and the like. Among them, dl-malic acid is preferred.

The proportions of the effervescent components in the composition of the invention are as follows: the proportion of sodium hydrogencarbonate and/or sodium carbonate is selected from the range of 10 to 35%, preferably 20 to 30%, and the proportion of the neutralizing agent is selected from the range of 10 to 70%, preferably 10 to 40%. In particular, a suitable proportion of sodium hydrogencarbonate is 10 to 35%, preferably 20 to 30%, and a suitable proportion of sodium carbonate is 11 to 31%, preferably 20 to 26%. It is the most desirable to use sodium hydrogencarbonate alone in a proportion selected from the range of 20 to 25%. The neutralizing agent is used preferably in at least equivalent amount relative to sodium hydrogencarbonate. The contemplated remarkable results of the invention can be achieved due to the presence of the effervescent components.

Stated more specifically, the presence of the effervescent components makes the composition of the invention highly soluble in water. A further advantage is that the solution of the composition in water shows good taste. However, if the sodium hydrogencarbonate and neutralizing agent are used in proportions outside said specific ranges, it would disadvantageously become difficult to produce an end product satisfactory in foaming property and taste.

Said effervescent components in conventional powder forms can be used in the present invention. The particle size (particle diameter, dimensions, etc.) of the particles is not specifically limited, but is preferably in the range which would not destroy the matrix of the antioxidant-containing powder in making the contemplated tablets. In other words, if the particles of high crystallinity are used as such, the matrix of the antioxidant-containing powder would be destroyed in making tablets so that the antioxidant would be likely to decompose and become lost on exposure to air, light, heat or the like. In this case, the effervescent components contribute to the destruction of the matrix depending on the inherent properties and crystallinity of respective effervescent components. The inventors' research found the following. When an organic acid is used as the neutralizing agent, large crystals of the acid should be pulverized and granulated before use. Particularly, when malic acid is used, it is the most desirable to use malic acid of 250 to 350 $\mu$m in average crystalline size which can be used without pulverization. For use as an excipient, large crystals of granulated sugar or the like are not desirable. Preferably used are a carbohydrate and the like pulverized and granulated as is the case with said neutralizing agent.

Generally sodium hydrogencarbonate and/or sodium carbonate having a particle size of 100 to 150 $\mu$m is preferred. For use as an excipient, the carbohydrate can be any of conventional saccharides such as glucose, fructose and like monosaccharides, maltose, sucrose and like disaccharides, xylitol, sorbitol, maltitol, mannitol, erythritol and like sugar alcohols, etc. Of these saccharides, maltitol, sorbitol and maltose are preferable. The particle size of these excipients can be the same as available powdery or granular crystals and is generally about 180 to about 350 $\mu$m although not specifically limited.

The proportions of the antioxidant-containing powder, effervescent components and excipient for use herein are essentially selected from the above specific ranges. Thereby the effervescent composition capable of achieving the contemplated results of the invention can be obtained. On the other hand, the proportion of the antioxidant-containing powder below said range would lead to a disadvantage that the obtained composition is deprived of commercial value, whereas the proportion of the antioxidant-containing powder above said range would result in disadvantages that the weight of tablets is increased and the solubility is impaired.

The effervescent composition of the invention essentially containing said predetermined amounts of the specific ingredients may contain additives conventionally used. Useful additives include, for example, thickeners, surfactants (emulsifiers), osmotic pressure regulators, electrolytes, sweeteners, flavor enhancers, pigments, pH adjusters, etc. The proportions of these additives are optional and are usually selected from the range which can produce the inherent effects of respective additives and which would not adversely affect the desired results of the invention.

The effervescent composition of the invention can be prepared by conventional processes using said essential components and optional additives. A preferred producing process is a dry low pressure tabletting process which comprises weighing out the components, mixing them and forming the mixture into tablets under a relatively low pressure. Too high a pressure for making a tablet would break the matrix of the antioxidant-containing powder, thereby making the antioxidant easily oxidizable, whereas too low a pressure would deteriorate the properties of the tablet. Hence, a useful pressure is selected from a proper range. The pressure is usually selected from the range of about 0.2 to about 0.35 ton/cm$^2$ preferably about 0.24 to about 0.31 ton/cm$^2$. It is recommendable that the pressure in said range result in tablets having hardness of about 4.0 to about 6.6 kp, preferably about 4.5 to about 5.9 kp. The hardness of the tablets is expressed in terms of a pressure under which the tablet was broken by compression of two sides at a specific loading speed (1.0 mm/sec) using a Schleuniger tablet hardness meter, Model 4M (Schleuniger-4M).

BEST MODE FOR CARRYING OUT THE INVENTION

Given below are Examples to clarify the present invention in more detail The parts and percentages in the Examples are all by weight.

EXAMPLE 1

| | |
|---|---|
| Granulated sugar | 2,000 mg |
| dl-Malic acid (the acid with an average particle size of 250 to 350 μm) | 1,000 mg |
| L-Ascorbic acid | 500 mg |
| Sodium hydrogencarbonate | 1,000 mg |
| β-Carotin powder (containing 4% β-carotin) | 50 mg |
| Sweetener | q.s. |
| Flavor enhancer | q.s. |
| Total | 4,800 mg |

The β-carotin powder was prepared by forming a matrix from 4 parts of β-carotin dissolved in 32 parts of vegetable fat and oil, 2 parts of L-ascorbic acid, 2 parts of tocopherol extract, 0.9 part of tea extract (containing tea polyphenol), 0.1 part of an ester of L-ascorbic acid with palmitic acid and 58 parts of arabic gum (saccharide) as a base material.

The above ingredients were mixed together and the mixture was formed into tablets of the invention under a pressure of 0.26 ton/cm$^2$.

The tablets thus obtained had hardness of 5.1 kp, took 1 minutes 10 seconds for dissolution and showed good stability (the ratio of residual β-carotin was 90% or a little higher in an accelerated test conducted after 2-week storage at 50° C.).

The hardness of tablets was measured by said method and the dissolution time was determined by dissolving the tablets in 140 cc of cold water (8° C.). The stability of β-carotin was evaluated by the following method. The β-carotin in the tablet was extracted with cyclohexane, and the absorption wavelength (450 nm) of the carotin in the extract was measured by an absorbance meter (Hitachi U-3000). The results were expressed in terms of a ratio of residual carotin with time based on the measurement values obtained immediately after production. The higher the value is, the less the loss of carotin due to the degradation by oxidation is. Other stability test items were conducted which were selected from the swelling of a packaging material (by visual inspection), discoloration of tablets (using a color difference meter, product of Tokyo Denshoku Co., Ltd., Color Ace Model TC-1), and the variation of taste (by a functional test).

The packaging material showed no swelling after 2-week storage at 50° C. The tablets exhibited a discoloration of ΔE value<3, and the variation of taste was within the allowable range.

EXAMPLES 2 to 7

Effervescent tablets were prepared according to the present invention from the components shown in Table 1 below (the unit of numerical values in the table is milligram).

TABLE 1

| | Ex. 2 | Ex. 3 | Ex. 4 | Ex. 5 | Ex. 6 | Ex. 7 |
|---|---|---|---|---|---|---|
| β-Carotin | 2 | 5 | | | | |
| Vitamin E | | | 5 | | 10 | |
| Tea polyphenol extract | | | | 10 | | 30 |
| Malic acid | 800 | 300 | | 500 | 1,000 | |
| Tartaric acid | | 300 | 1,000 | | | |
| Citric acid | | 300 | | 300 | | 1,000 |
| L-Ascorbic acid | 100 | 500 | 100 | 200 | | |
| Sodium hydrogen-carbonate | 900 | | 500 | 1,000 | | 700 |
| Sodium carbonate | | 1,000 | 500 | | 1,000 | 200 |
| Frost sugar | 2,000 | 2,300 | 2,000 | 2,500 | 2,000 | 2,200 |
| Vegetable fat and oil | 10 | 10 | 20 | 15 | 10 | 0 |
| Gum arabic | 20 | 25 | 15 | 10 | 10 | 12 |
| Sweetener | q.s. | q.s. | q.s. | q.s. | q.s. | q.s. |
| Flavor enhancer | q.s. | q.s. | q.s. | q.s. | q.s. | q.s. |
| Other components | q.s. | q.s. | q.s. | q.s. | q.s. | q.s. |
| Total (per tablet) | 4,500 | 5,200 | 4,600 | 5,500 | 4,600 | 4,800 |

EXAMPLES 8 to 20

Effervescent tablets were prepared according to be present invention from the components shown in Tables 2 and 3 below (numerical values in Tables 2 and 3 are by wt. %).

TABLE 2

| | Example No. | | | | | | |
|---|---|---|---|---|---|---|---|
| | 8 | 9 | 10 | 11 | 12 | 13 | 14 |
| Granulated sugar | — | — | — | — | — | — | — |
| Frost sugar | 42 | 42 | 42 | 42 | 41 | 41 | 42 |
| Glucose | — | — | — | — | — | — | — |
| Fructose | — | — | — | — | — | — | — |

TABLE 2-continued

| | Example No. | | | | | | |
|---|---|---|---|---|---|---|---|
| | 8 | 9 | 10 | 11 | 12 | 13 | 14 |
| L-Ascorbic acid | 10 | 10 | 10 | 10 | 10 | 10 | — |
| L-Tartaric acid (granules) | — | — | — | — | 25 | — | — |
| Citric acid (granules) | — | — | — | — | — | 25 | 30 |
| dl-Malic acid | 21 | 21 | 21 | 21 | — | — | — |
| Sweetener | q.s. | q.s. | q.s. | q.s. | q.s. | q.s. | q.s. |
| Sodium hydrogencarbonate | 21 | 21 | 21 | 21 | 20 | 20 | 21 |
| Sodium carbonate | — | — | — | — | — | — | — |
| fl-Carotin powder | 1.1 | 2.2 | 0.5 | 0.7 | 1.0 | 1.0 | 1.1 |
| Flavor enhancer/pigment | Trace | Trace | Trace | Trace | Trace | Trace | Trace |
| Potassium carbonate | — | — | — | — | — | — | — |
| Weight (g/tablet) | 4.8 | 4.8 | 4.8 | 4.8 | 5.1 | 5.1 | 4.8 |
| β-Carotin content (mg/tablet) | 2 | 4 | 1 | 3 | 2 | 2 | 2 |

TABLE 3

| | Example No. | | | | | |
|---|---|---|---|---|---|---|
| | 15 | 16 | 17 | 18 | 19 | 20 |
| Granulated sugar | — | — | — | 42 | — | — |
| Frost sugar | 36 | 42 | 42 | — | — | — |
| Glucose | — | — | — | — | 42 | — |
| Fructose | — | — | — | — | — | 42 |
| L-Ascorbic acid | 8 | 10 | 10 | 10 | 10 | 10 |
| L-Tartaric acid (granules) | — | — | — | — | — | — |
| Citric acid (granules) | — | — | — | — | — | — |
| dl-Malic acid | 31 | 22 | 21 | 21 | 21 | 21 |
| Sweetener | q.s. | q.s. | q.s. | q.s. | q.s. | q.s. |
| Sodium hydrogencarbonate | 21 | 17 | 21 | 21 | 21 | 21 |
| Sodium carbonate | — | 4 | — | — | — | — |
| β-Carotin powder | 0.9 | 1.1 | 1.1 | 1.1 | 1.1 | 1.1 |
| Flavor enhancer/pigment | Trace | Trace | Trace | Trace | Trace | Trace |
| Potassium carbonate | — | — | — | — | — | — |
| Weight (g/tablet) | 5.8 | 5.0 | 5.0 | 4.8 | 4.8 | 4.8 |
| β-Carotin content (mg/tablet) | 2 | 2 | 2 | 2 | 2 | 2 |

EXAMPLES 21 to 26

Effervescent tablets were prepared according to the present invention from the components shown in Table 4 below (numerical values in the table are by wt. %).

TABLE 4

| | Example No. | | | | | |
|---|---|---|---|---|---|---|
| | 21 | 22 | 23 | 24 | 25 | 26 |
| Granulated sugar | 20 | 20 | 31 | 35 | 20 | 20 |
| Maltitol | 18 | 18 | 6 | 1 | — | — |
| Sorbitol | — | — | — | — | 18 | — |
| Maltose | — | — | — | — | — | 18 |
| L-Ascorbic acid | 10 | 10 | 10 | 10 | 10 | 10 |
| L-Tartaric acid | 20 | — | 20 | 21 | 20 | 20 |
| Citric acid | — | 20 | — | — | — | — |
| Sweetener | q.s. | q.s. | q.s. | q.s. | q.s. | q.s. |
| Sodium hydrogencarbonate | 20 | 20 | 20 | 18 | 20 | 20 |
| Sodium carbonate | — | — | — | 2 | — | — |
| β-Carotin powder | 1.1 | 1.1 | 1.1 | 1.1 | 1.1 | 1.1 |
| Flavor enhancer/pigment | Trace | Trace | Trace | Trace | Trace | Trace |
| Weight (g/tablet) | 5.1 | 5.1 | 5.i | 5.1 | 5.1 | 5.1 |
| β-Carotin content (mg/tablet) | 2 | 2 | 2 | 2 | 2 | 2 |

Effervescent tablets were prepared according to the present invention in the same manner as in Example 21 with the exception of varying the proportions of granulated sugar and maltitol as a carbohydrate and making tablets by altering the pressure until the tablets showed the same numerical value of hardness.

The pressures for making tablets and the time taken for dissolution were determined in respect of each obtained tablet.

The results are shown below, together with the amount of the carbohydrate used, in Table 5.

TABLE 5

| | Carbohydrate used | | Pressure for making tablets | Dissolu- |
|---|---|---|---|---|
| Speci-men No. | Granulated sugar | Maltitol | (ton/25 mm Ø) | tion time |
| 1 | 1,900 mg | 0 | 3.9 | 2 min. 10 sec. |
| 2 | 1,600 mg | 300 mg | 3.0 | 2 min. 00 sec. |
| 3 | 1,300 mg | 600 mg | 2.0 | 1 min. 44 sec. |
| 4 | 1,000 mg | 900 mg | 1.6 | 1 min. 27 sec. |

Table 5 shows that the more the amount of maltitol is, the lower the pressure for making tablets is and the shorter the dissolution time is.

Possibility of Industrial Application of the Invention

According to the present invention, there is provided an epoch-making composition which stably contains an antioxidant, has high tablet hardness and can be dissolved in a short time. The composition of the invention is useful in the food field and the pharmaceutical field.

What we claim is:

1. An antioxidant-containing dry effervescent composition consisting essentially of:

0.05 to 15% by weight of an antioxidant-containing powder containing 0.2 to 20% by weight, based on the antioxidant-containing powder, of at least one antioxidant selected from the group consisting of carotin and catechin, 10 to 35% by weight of sodium hydrogencarbonate and/or sodium carbonate, 10 to 70% by weight of at least one pH neutralizing agent selected from the group consisting of L-tartaric acid, citric acid, lactic acid, dl-malic acid, fumaric acid and L-ascorbic acid, and 30 to 55% by weight of an excipient.

2. The antioxidant-containing dry effervescent composition according to claim 1 which consists essentially of:

0.1 to 5.0% by weight of an antioxidant-containing powder containing 0.5 to 10% by weight, based on the antioxidant-containing powder, of at least one antioxidant selected from the group consisting of carotin and catechin, 20 to 30% by weight of sodium hydrogencarbonate and/or sodium carbonate, 10 to 40% by weight of at least one pH neutralizing agent selected from the group consisting of L-tartaric acid, citric acid, lactic acid, dl-malic acid, fumaric acid and L-ascorbic acid, and 30 to 55% by weight of an excipient.

3. The antioxidant-containing effervescent dry composition according to claims 1 to 2, wherein the excipeint is a carbohydrate selected from maltitol, sorbitol and maltose.

4. A catechin-containing dry effervescent composition consisting essentially of:

0.05 to 15% by weight of a catechin-containing powder containing at least 10% by weight, based on the catechin-containing powder, of catechin, 10 to 35% by weight of sodium hydrogencarbonate and/or sodium carbonate, 10 to 70% by weight of at least one pH neutralizing agent selected from the group consisting of L-tartaric acid, citric acid, lactic acid, dl-malic acid, fumaric acid and L-ascorbic acid, and 30 to 55% by weight of an excipient.

5. The antioxidant-containing dry effervescent composition according to claim 1 or 2, wherein said sodium hydrogencarbonate and/or sodium carbonate have a particle size of 100 to 150 $\mu$m.

6. The catechin-containing dry effervescent composition according to claim 4, wherein said sodium hydrogencarbonate and/or sodium carbonate have a particle size of 100 to 150 $\mu$m.

* * * * *